United States Patent
Bock et al.

(10) Patent No.: US 11,568,569 B2
(45) Date of Patent: Jan. 31, 2023

(54) METHOD AND DEVICE FOR DETERMINING THE HOMOGENEITY OF SKIN COLOR

(71) Applicant: Henkel AG & Co. KGaA, Duesseldorf (DE)

(72) Inventors: Andreas Bock, Neuss (DE); Georg Knuebel, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 399 days.

(21) Appl. No.: 16/481,921

(22) PCT Filed: Feb. 14, 2018

(86) PCT No.: PCT/EP2018/053673
§ 371 (c)(1),
(2) Date: Jul. 30, 2019

(87) PCT Pub. No.: WO2018/149874
PCT Pub. Date: Aug. 23, 2018

(65) Prior Publication Data
US 2021/0358172 A1 Nov. 18, 2021

(30) Foreign Application Priority Data
Feb. 20, 2017 (DE) .................. 10 2017 202 702.9

(51) Int. Cl.
G06T 7/90 (2017.01)
G06T 7/00 (2017.01)

(52) U.S. Cl.
CPC .............. *G06T 7/90* (2017.01); *G06T 7/0012* (2013.01); *G06T 2207/10024* (2013.01); *G06T 2207/30088* (2013.01)

(58) Field of Classification Search
CPC ............. G06T 7/90; G06T 7/0012; G06T 2207/10024
See application file for complete search history.

(56) References Cited

U.S. PATENT DOCUMENTS

| | | |
|---|---|---|
| 2002/0048399 A1 | 4/2002 | Lee et al. |
| 2004/0218810 A1 | 11/2004 | Momma |
| 2006/0126941 A1* | 6/2006 | Higaki ................ G06V 40/103 382/103 |
| 2007/0058858 A1 | 3/2007 | Harville et al. |
| 2007/0064985 A1 | 3/2007 | Chhibber et al. |
| 2007/0086651 A1 | 4/2007 | Stephan et al. |
| 2010/0185064 A1* | 7/2010 | Bandic ................ A61B 5/444 600/306 |
| 2013/0343647 A1 | 12/2013 | Aoki |
| 2014/0304629 A1 | 10/2014 | Cummins et al. |
| 2018/0089856 A1* | 3/2018 | Sato ................ H04N 1/628 |
| 2018/0139359 A1* | 5/2018 | Lesellier .............. H04N 1/6005 |
| 2018/0197226 A1* | 7/2018 | Kobayashi .............. G06T 11/60 |

FOREIGN PATENT DOCUMENTS

JP 2005293555 A * 10/2005 ......... G06K 9/00234

OTHER PUBLICATIONS

EPO, International Search Report issued in International Application No. PCT/EP2018/053673, dated May 9, 2018.
Fink et al.: "Colour homogeneity and visual perception of age, health and attractiveness of male facial skin", Journal of the European Academy Dermatology Venereology 2012, 26, 1486-1492.
Tsuruoka Shinji, et al., Skin Color Area Extraction for Gesture Analysis from Digital Video Movies, Aug. 31, 2016, XP055950928, URI: https://www.researchgate.net/profile/Kumiko-Obara/publication/309348416_Skin_Color_Area_Extraction_for_Gesture_Analysis_From_Digital_Video_MOVIES/links/581177c208aea04bbcbd55e3/SKIN-COLOR-AREA-EXTRACTION-FOR-GESTURE-ANALYSIS-FROM-DIGITAL-VIDEO-MOVIES.pdf.
Philipp Berens, CircStat: A MATLAB Toolbox for Circular Statistics, Journal of Statistical Software, Sep. 1, 2009, XP055238648, URL: http://kyb.mpg.de/fileadmin/user_upload/files/publications/attachments/J-Stat-Softw-2009-Berens_6037[0].pdf.
Allan Hanbury, Circular Statistics Applied to Colour Images, Computer Vision Workshop, XX, XX, Nr. 8th, Feb. 3, 2003, pp. 1-6, XP002393138.

\* cited by examiner

*Primary Examiner* — Santiago Garcia
*Assistant Examiner* — Winta Gebreslassie
(74) *Attorney, Agent, or Firm* — Lorenz & Kopf, LLP

(57) ABSTRACT

In various embodiments, a method for determining a homogeneity of complexion is provided. The method may include provision of a digital image on which skin is portrayed and which is parameterized in a color space which is defined by a parameter set in which one of the parameters is a hue, identifying and/or defining at least one skin examination area in the transformed image, calculating a hue distribution in the at least one skin examination area, and determining at least one homogeneity value for the complexion based on the calculated hue distribution.

14 Claims, No Drawings

METHOD AND DEVICE FOR DETERMINING THE HOMOGENEITY OF SKIN COLOR

CROSS REFERENCE TO RELATED APPLICATIONS

This application is a U.S. National-Stage entry under 35 U.S.C. 35 U.S.C. § 371 based on International Application No. PCT/EP2018/053673, filed Feb. 14, 2018, which was published under PCT Article 21(2) and which claims priority to German Application No. 10 2017 202 702.9, filed Feb. 20, 2017, which are all hereby incorporated in their entirety by reference.

TECHNICAL FIELD

The present disclosure relates to a method and an apparatus for determining a homogeneity of skin color.

BACKGROUND

Healthy skin and a homogeneous facial coloring are generally considered attractive. However, with advancing age and/or as a result of sun damage, many people experience changes to their skin such as red patches or yellowish-brown discolorations. Particularly redness and/or discolorations of the face, which are immediately evident to anyone, are perceived as unpleasant by those affected.

From a medical perspective, most instances of reddened patches on the face are entirely inconsequential. For the most part, even skin disorders such as rosacea represent only a cosmetic problem. Rosacea is a relatively widespread facial skin disorder, the early form of which is often also called Couperosa. The exact causes of rosacea are not known, though genetic predisposition does seem to play an important part. Then, factors such as excessive sunbathing, high blood pressure, gastric and intestinal disorders, climatic effects, alcohol, nicotine and coffee may lead to an exacerbation. The early form of rosacea is characterized by reddish patches on the face, small bluish-red veins becoming visible through the skin and sensitive facial skin. The physical manifestations of advanced stages are quite similar to acne vulgaris, advance in phases and are characterized by tender pustules and papules.

Brownish discolorations of the skin may have entirely natural causes, and include for example freckles, liver spots or moles. These "color defects"—also referred to as pigment spots—are caused primarily by overproduction of the pigment melanin. One well-known example of a cause of stimulated melanin production is sunlight, or the UV radiation it contains. This also bears significant responsibility for the appearance of age spots (Lentigo solaris, Lentigo senilis). Internal factors such as physical age, metabolism, hormones or taking certain medications also contribute.

White patches on the skin (Vitiligo or leukoderma) appear because the skin cells that are responsible for producing skin pigment (melanocytes) die or are at least inactivated.

Various special cleansing and/or care products are available for treating reddened skin on the face and/or body. Skin whitening creams or solutions can be helpful in alleviating or removing brownish discolorations.

For some time, there has been a trend in many areas of daily life towards personalised programmes and/or products which are able to selectively address individual conditions and needs, in the realm of nutrition or health, for example.

Without specialised dermatological or cosmetic advice, many users may find it difficult to determine their individual skin condition and the cosmetics that are suitable for their skin condition.

It is also difficult for a user to objectively monitor and assess the success of the treatment, and therewith the efficacy of skin care products, particularly in terms of the reduction of redness and/or or discolorations. As a consequence, the motivation to complete a thorough care or and/or treatment programme regularly and rigorously may diminish.

The homogeneity of a user's skin color or complexion can be in important parameter for the consumer's purposes.

A quantitative measure for an assessment of the homogeneity of a skin color or complexion, and particularly for an assessment of how the homogeneity of a user's skin color or complexion develops over time can be desirable.

SUMMARY

One object of the present disclosure was to provide a method for determining a homogeneity of a user's skin color or complexion.

This object is solved with a method for determining a homogeneity of a user's skin color including:
  providing a digital image, on which skin is portrayed and which is parameterised in a color space which is defined by a parameter set in which one of the parameters is a hue;
  identifying and/or defining at least one skin examination area in the digital image;
  calculating a hue distribution in the at least one skin examination area; and
  determining at least one homogeneity value for the complexion based on the calculated hue distribution.

In various embodiments, a homogeneity of complexion may serve as a target parameter, which may be determined by subsequent statistical analysis of a hue angle.

In various embodiments, it may be possible to perform the method for calculating the homogeneity of complexion with only little or no technical equipment. For example, it may be possible to perform the method using an app on a tablet, a laptop or a smartphone. Accordingly, the app may be a "mobile app" (application software for mobile devices), a web app (application software according to the client-server model) or a desktop app (application software for a desktop computer).

The method may for example enable a user to determine the homogeneity of his/her complexion, e.g., in the face, even without professional assistance and without having to provide a skin sample for manipulation, by using a smartphone, laptop or tablet for example to capture a digital image of the skin and determine a homogeneity of complexion by the smartphone/tablet/laptop, wherein the smartphone/tablet/laptop may be used in various embodiments to provide the image to an external data processing apparatus, e.g., a cloud, and to receive the results calculated there and display them to the user.

In various embodiments, the provision of the digital image may include transformation of an original digital image which has been parameterized in an original color space into the color space, wherein the original color space may differ from the color space.

In various embodiments, the provision of the digital image may include reading the image that has been parameterized in the color space, for example reading from a camera with which the digital image was captured.

In various embodiments, the color space may be a hue-saturation-brightness color space.

In various embodiments, the hue may be defined by a color angle on a color circle.

In various embodiments, the calculation of at least one homogeneity value of the complexion based on the determined hue distribution may include determining a circular variance.

In various embodiments, the identification and/or definition of at least one skin examination area may include defining the at least one skin examination area by a user.

In various embodiments, the definition of the at least one skin examination area by the user may include defining a position and/or shape and/or size of the skin examination area.

In various embodiments, the identification and/or definition of at least one skin examination area may include determination of a skin display area, in which the skin is displayed, and definition of at least a part of the skin display area as the at least one skin examination area.

In various embodiments, the at least one skin examination area may include a plurality of skin examination areas.

In various embodiments, the plurality of skin examination areas may differ from each other in terms of the position of their central points.

In various embodiments, the method may further include correlation of the calculated color homogeneity value with the positions of the central points of the skin examination areas.

In this way, for example a spatial distribution of the homogeneity of the complexion may be determined, for example in the case of an inhomogeneous hue distribution areas of the skin may be identified which exhibit particularly high inhomogeneity. In various embodiments, these areas may be subjected to special treatment or—if the determination of the homogeneity of the skin tone is carried out after a one-time or repeated care and/or cleansing treatment—or undergo a follow-up treatment.

In various embodiments, the method may further include displaying the calculated result.

In various embodiments, the display of the calculated result may include display of the digital image, wherein the skin is displayed with the hue in the skin display area of the digital image, wherein the total skin display area is represented with a uniform color saturation and a uniform brightness.

In various embodiments, the method may further include display of an individual guide.

In various embodiments, an apparatus for determining a homogeneity of complexion is provided. The device may include a data processing apparatus and a display apparatus and may be configured to perform the method for determining a homogeneity of complexion.

In various embodiments, the data processing apparatus and the display apparatus may be part of a smartphone, a laptop or a tablet. It is preferred that the data processing apparatus and the display apparatus are part of a smartphone or tablet.

In various embodiments, the apparatus may be configured to perform the method according to various embodiments by an app.

In various embodiments, an individual guide may be provided on the basis of the determined homogeneity of complexion. The individual guide may comprise for example product recommendations for care and/or cleansing products adjusted individually for the user and/or individual care and/or cleansing instructions. The product and/or cleansing recommendations and/or care and/or cleansing instructions may be provided for example by a software program, e.g., an app. Additionally, a recommended product may be offered to the user for purchase, and the user may initiate the purchase by making an entry. Besides the purchase of products, further information may be offered to the user for purchase. Such further information may refer to more detailed individual care and/or cleansing instructions. For example, the software/app program receives the request to the effect that the user would like to purchase the recommended product, stores the request and/or transmits the request to a trading company which markets the product. The user is prompted to enter his/her personal data (address, bank information, preferred shipping method, etc.) by the software/app. Alternatively, the user may be informed where the recommended product can be purchased (for example, chemist's shop, beauty parlour, perfumery, pharmacy, etc.).

In various embodiments, the software/app which determines the homogeneity of complexion may be the same as the one which determines the product and/or cleansing recommendation and/or the care and/or cleansing instructions and/or initiates an order process. In various embodiments, different software programs/apps may be used for some of the various processes or for all of the different processes (determining the homogeneity of the complexion, determining a product and/or cleansing recommendation, determining a set of care and/or cleansing instructions) and/or initiating an order process.

The individual guide may comprise product recommendations for care and/or cleansing products manufactured individually for the user. For example, in various embodiments an order process may be initiated by the software/app which determines the homogeneity of complexion, or by a further software/app, preferably by calling a website of a manufacturer of individual care and/or cleansing products.

The individual care and/or cleansing products may be a product that has been manufactured especially for the user or a "mass customized" product. In the case of a "mass customized" product, an individualization may be created by varying a small number of features of a care and/or cleansing product which are however critical from the user's point of view. These "mass customized" products are preferably based on the concept of modularization, which means that the care and/or cleansing product may be assembled individually from various modules/building blocks.

There are often a large number of dependencies between the many different features/constituents of a products, which may be expressed as "mandatory inclusions" or "prohibitions". In order to obtain an unambiguous product definition, it may be advantageous if the order process is executed with the aid of a product configurator. This configurator assists the user in selecting the features/constituents and makes him/her aware of the permitted/forbidden feature combinations, wherein the latter then cannot be selected.

In care and/or cleansing products for the skin, the pertinent product features particularly include the chemical constituents of the agents, the physical properties of the agents and the nature of the combination of the agents. With the aid of a product configurator, for example, the selection of chemically and/or physically incompatible constituents or the selection of constituents that are unsuitable for the may be avoided. Conversely, the selection of constituents suitable for the determined homogeneity of complexion may be prescribed or proposed by the product configurator.

It is also preferred that the composition of the individual care and/or cleansing products is stored and used for a long-term recommendation in subsequent methods.

A low homogeneity value of the complexion indicates the existence of many discolorations, that is to say for example areas of redness, pigment spots, white spots or the like in/on the skin.

In the case of (very) pronounced rednesses, particularly in the case of rosacea, the individual guide may comprise the recommendation of care and/or cleansing products with antibiotics, such as metronidazole, azelaic acid, tetracycline and clindamycin for example.

In the case of (very) pronounced rednesses, particularly in the case of Couperosa, the individual guide may comprise the recommendation of care and/or cleansing products with constituents which result in a strengthening of the skin's protective barrier and of the vulnerable vessels. Examples include ruscus, aescin, lady's mantle, horse chestnut, ginkgo, red vine leaves, dextran, liquorice extract, allantoin, bisabolol, ivy, glycerin, aloe vera or shea butter.

Alternatively, the individual guide may the recommendation of care and/or cleansing products which are free from certain constituents. These care and/or cleansing products contain for example allergen-free fragrance (free from allergens that are listed in the Cosmetics Ordinance), no photosensitizing substances, no parabens, no essential oils, no synthetic pigments and only a minimum quantity of preservatives.

In the case of mild rednesses, the individual guide may include the recommendation of care and/or cleansing products with green pigments, which neutralise the appearance of redness.

In the case of yellowish-brown discolorations, for example pigment spots, the individual guide may include the recommendation of care and/or cleansing products with hydroquinone, azelain, watercress extracts and/or vitamin C as lightening agents.

In the case of pale discolorations, for example white spots (vitiligo), the individual guide may container the recommendation of care and/or cleansing products with cortisone, calcipotriol and/or pseudocatalase as the active ingredient.

In various embodiments, therapeutic success in the case of a cosmetic treatment which may have the objective of effecting a positive change on the determined homogeneity of the complexion may be monitored. In various embodiments, the software/app may enable monitoring and/or tracking of the results by a display (e.g., a graphical display) of the measurement results over time.

In various embodiments, additional information relating to a general state of health, further skin condition parameters, dietary habits and other behaviours of the user (e.g., amount of time per day spent outdoors/in the sun/in the water, smoking habits, medications taken etc.) may be used, e.g., via the software/app in the course of identifying the product and care recommendations. The user's personal information such as age, weight or sex may also be used when determining the product and care recommendations.

In various embodiments, literature data for assessing a suitability of a care product and/or a care instruction for caring for a skin with a given homogeneity of the complexion may be based on literature data.

A care product and/or care instruction may be assessed as suitable for a homogeneity value, if it is to be expected, e.g., on the basis of the literature data, trial results or empirical values, that the homogeneity value of the user's complexion will be maintained or improved with (e.g., regular) application of the care products and/or the care instructions.

In various embodiments, an assessment of a suitability of a care product for improving the homogeneity of a user's complexion may be confirmed or modified by collecting experience values from other users with the same or a similar skin condition, for example empirical values relating to a treatment success. In this way, it may be made possible that the user always receives an optimal recommendation.

In various embodiments, an effectiveness of a (e.g., cosmetic) treatment may be verified better and thereby a selection of an individually suitable product may be or become simplified.

In various embodiments, a user's motivation for carrying out a cosmetic treatment for a prolonged period may be increased for example by a comparison with other users, e.g., using information about treatment successes provided by other users.

In various embodiments, a consultation with a dermatologist or cosmetician may be recommended for example in the case of very low homogeneity values of the complexion. In various embodiments, a procedure for making an appointment may be initiated directly via the software/app that determines the homogeneity of the complexion. For this purpose, the contact information of dermatologists and/or cosmeticians may be stored in the software/app for example and displayed to the user. In addition, the selection may be restricted by filters, such as the postal code, for example. In various embodiments, an appointment may be booked directly via the software/app. Alternatively, an appointment with a dermatologist and/or cosmetician may be made via a separate software/app, such as Treatwell, for example.

The method for determining a homogeneity of complexion may particularly be carried out by a user in a private setting. Alternatively, the method for determining a homogeneity of complexion may be performed by another person, for example at the point of sale of care and/or cleansing products for the skin or in the course of a consultation with a dermatologist or cosmetician. In this case, the user is the person examined.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Embodiments of the present disclosure are explained in greater detail in the following text.

Of course, other embodiments may be used and structural or logical changes may be made without departing from the scope of protection of the present disclosure. It is understood that the features of the various exemplary embodiments described herein may be combined with each other unless specifically stated otherwise. The following detailed description is therefore not to be considered limiting in nature, and the scope of protection of the present disclosure is defined by the accompanying claims.

A first object of the present disclosure is a method for determining a homogeneity of complexion, including: providing a digital image, on which skin is portrayed and which is parameterized in a color space that is defined by a parameter set in which one of the parameters is a hue; identifying and/or defining at least one skin examination area in the digital image; calculating a hue distribution in the at least one skin examination area; and determining at least one homogeneity value for the complexion based on the calculated hue distribution.

In this context, a digital image may be understood to be a data package which may be represented by a data processing system as a two-dimensional (flat) array of picture elements (also called pixels), in a coordinate system, for example, which has an x-axis and a y-axis, wherein each pixel has at least one image position as an x,y coordinate pair and an element of intensity information, wherein the intensity information may be represented for example as a color of a pixel on a monitor or of a printed dot in a hardcopy image. The digital image may be for example a photograph taken with a digital camera or a single frame from a video sequence recorded with a digital camera.

In this context, a "color" may describe an interplay between a hue (i.e. a spectral color impression, which may be understood to be that which is perceived as the "actual color"), a color intensity (i.e. how intense the color appears, e.g., compared with a neutral grey, which is also referred to as saturation, color saturation, coloration, chromaticity or color depth) and a brightness or darkness (i.e. how bright or dark the color appears to be).

For a color representation, the color may be parameterized in a color space.

A common color space, from which color information (e.g., color information of the skin) originates or in which the color information is represented may be structured in such manner that a determined or represented color is independent of a medium by which the color is determined or represented (e.g., colorimeter, monitor, printer, scanner, human eye, etc.). The color space may be a L*a*b* color space, for example. In this context, the hue may be parameterised for example by two parameters, a* and b*.

Other usual color spaces may be for example an RGB (parameterised in Red, Green, Blue) or CIELUV (in this case the hue is parameterised in a u-v plane) color space, which may be more suitable for an additive luminous color as is used in monitors, for example, than the L*a*b* color space, for example, or a CMYK color space, which is based on a subtractive color model and is used in particular in full color printing applications and parameterizes colors in four color channels Cyan, Magenta, Yellow and black (color depth, Key) corresponding to the basic printing colors.

Conversion to HSV values (or to other color spaces that define a color angle, e.g., HSB, LCh) makes it possible to achieve complete separation of the hue information (hue) from the brightness information, which in turn enables the color homogeneity to be considered in isolation.

In various embodiments, the distribution of hue values may be used to determine at least one color homogeneity value.

Statistical test methods may be used to calculate for example a standard deviation, also called a confidence interval d, a circular variance S and/or an angular deviation s of the hue distribution.

In color spaces that include the hue as a parameter in its own right and which can be used according to various embodiments in the method for determining a homogeneity of complexion, the hue is expressed as an angle that can be greater than or equal to 0° and less than about 360°.

Therefore, in various embodiments for the statistical test of hue distribution, a circular statistical system may be used. Among other advantages, with the aid of the circular statistical system it may be possible to avoid inhomogeneities during a transition from about 359° to about 0° (if the usual linear statistical method were used, such inhomogeneities would result in an average of about 10° and about 350° of about 180° instead of the logical value of about 0°).

In various embodiments, angles $\alpha_i$ assigned to the hues may first be converted into unit vectors in a two-dimensional plane using $$r_i = \begin{pmatrix} \cos \alpha_i \\ \sin \alpha_i \end{pmatrix}.$$

In order to obtain an average angle $\overline{\alpha}$, in various embodiments the unit vectors may be calculated:

$$\overline{r} = \frac{1}{N} \sum_i r_i$$

The average angle $\overline{\alpha}$ may be calculated from the averaged vector $\overline{r}$, optionally with specification of a confidence interval, e.g., a 95% by conversion using the four quadrant inverse tangent function.

A vector length $$R = \|\overline{r}\|,$$

which may have a value between 0 and 1, may already represent a dimension for the color homogeneity of the skin, because the greater the color homogeneity is, the closer the angles assigned to the hues are located to each other, and consequently the longer vector length R may be (i.e. accordingly closer to 1).

In various embodiments a circular variance $$S = 1 - R$$

may serve as a measure of color homogeneity. This also lies between 0 and 1, although in this case the closer the angles are to each other, the smaller it is.

In various embodiments an angular standard deviation (also called angular deviation)

$$S = \sqrt{2(1-R)}$$

may also be used as a measure of color homogeneity.

In addition, other values known in circular statistics which return a measurement for a distribution, e.g., scattering of the hues, may also be used.

Circular statistics may be calculated with any suitable software program, for example using a software specially manufactured for the purpose, e.g., an app, or for example with the aid of existing software packages, e.g., Oriana or the EXCEL tool EZ-Rose.

A skin display area, i.e., an area in which skin is imaged, may be determined using known methods. The known method may include a cropping method, for example, such as may be used commonly in Photoshop and other software packages, for example.

The skin display area may include a plurality of pixels of a digital image which depict the skin and may form an area which is either contiguous or includes a plurality of single areas. One plane in which the skin area may be arranged may be defined by the x-axis and the y-axis of the digital image for example.

In various embodiments, at least one skin examination area may be identified or defined in the digital image.

In various embodiments, the skin examination area may include a partial area of the skin display area.

In various embodiments, the digital image may also include further display areas in addition to the skin display area, in which for example objects, body parts etc. may be displayed. In various embodiments, the skin examination area may be selected such that no part of the other display areas falls within the skin examination area.

In various embodiments the skin examination area may be of any shape, for example, apart from rectangular (e.g., square) the skin examination area may also be triangular, polygonal with a number of angles other than three or four, elliptical, round, or of any other shape. For example, the skin examination area may include the entire skin display area.

In various embodiments in which the skin examination area includes the entire skin display area, the skin examination area may thus include a single-part or a multi-part area, which may be examined as a single skin examination area—also in the case of the multi-part area—for subsequent analysis, e.g., for calculating a value of a proportion of linear areas and/or for a distribution or linear areas.

In various embodiments, the at least one skin examination area may include a plurality of skin examination areas. In various embodiments, in a subsequent analysis, e.g., when calculating a color homogeneity value, each of the plurality of skin examination areas may be examined separately, i.e., the value for the homogeneity of complexion may be calculated separately for each of the plurality of skin examination areas.

In various embodiments, the determination of the at least one skin examination area may include identification of the skin display area and definition of the at least one skin examination area.

Definition of the at least one skin examination area may mean for example that, as described previously, the entire skin display area is defined as the skin examination area, and/or single or multiple skin examination area(s) may be defined by automated features, for example with the aid of the data processing apparatus, e.g., taking into account preset conditions. For example, a size, position and/or number of the skin examination areas may be prescribed e.g., by a user, and the skin examination areas may then be defined by automated features, e.g., by a suitable software program, for example, in such manner that a minimum spacing is always assured between the skin examination areas, the skin display area is covered as evenly as possible, that the same skin examination areas are always selected, and so on.

In various embodiments, the homogeneity of complexion may be calculated as a function of time, for example a change in the color homogeneity over time may be determined, for example in certain temporal intervals following a care and/or cleansing treatment or the like.

In various embodiments, the hue channel may be displayed, to a user for example, by a display, for example.

In various embodiments, the hue channel (hue) may be transformed back into a color space which is suitable for the display (e.g., RGB for a monitor or CMYK for a printer) while suppressing the other channels (saturation, value), so possibly only the differences of the hue contribute to a different representation of various pixels, but a realistic representation may be obtained with regard to hues and the distances between the different hues.

In various embodiments, different hues which do not match the hues calculated may be assigned to the various hues of the hue channel for a display (in other words assigned to the various hue values of the hue parameter). In this way, it becomes possible to exaggerated small hue differences for the purposes of display, for example.

A possible conversion from RGB to HSV may be described as follows:

Precondition: $R, G, B \in [0, 1]$

-continued $\text{MAX} := \max(R, G, B), \text{MIN} := \min(R, G, B)$ $$H := \begin{cases} 0, & \text{if MAX} = \text{MIN} \Leftrightarrow R = G = B \\ 60° \cdot \left(0 + \frac{G-B}{\text{MAX}-\text{MIN}}\right), & \text{if MAX} = R \\ 60° \cdot \left(2 + \frac{B-R}{\text{MAX}-\text{MIN}}\right), & \text{if MAX} = G \\ 60° \cdot \left(4 + \frac{R-G}{\text{MAX}-\text{MIN}}\right), & \text{if MAX} = B \end{cases}$$

if $H < 0°$, then $H := H + 360°$ $$S_{HSV} := \begin{cases} 0, & \text{if MAX} = 0 \Leftrightarrow R = G = B = 0 \\ \frac{\text{MAX}-\text{MIN}}{\text{MAX}}, & \text{otherwise} \end{cases}$$

$$S_{HSL} := \begin{cases} 0, & \text{if MAX} = 0 \Leftrightarrow R = G = B = 0 \\ 0, & \text{if MAX} = 1 \Leftrightarrow R = G = B = 0 \\ \frac{\text{MAX}-\text{MIN}}{1-[\text{MAX}+\text{MIN}-1]}, & \text{otherwise} \end{cases}$$

$V := \text{MAX}$ $L := \frac{\text{MAX}+\text{MIN}}{2}$

Post-condition: $H \in [0°, 360°], S, V, L \in [0, 1]$

These formulas may reflect some particularities of the HSV values. For example, if R=G=B, H may be insignificant, with the result that by definition H=0 is set. If R=G=B=0, then S may be insignificant, with the result that by definition S=0 is set.

In various embodiments, modified color models, for example HSL, HSB or HSI, may be used instead of HSV.

The HSL color space (also referred to as HLS) may include the parameters hue (also referred to as color angle) H, color saturation S and color brightness L. Unlike the HSV color space, however, it may be also referenced on the grey point located between white and black as neutral grey. The pigment may be represented as a double cone, a cylinder or a hexagonal prism. In this context, the hues (chromatic values) may lie outside, and the grey point in the middle. The CIE-LCh° model with color brightness L, color saturation (chroma) C and the hue angle h° may be structured similarly, so that it may correspond to a certain degree to a Lab color space represented in cylinder coordinates.

The HSB and HSI models may be orientated towards the needs of colorimetry and phototechnical reproduction. In this case too, H may stand for hue and S for saturation. The difference may be related to the third coordinate: on the one hand HSB with the radiation measurement of brightness, e.g., the absolute brightness, B, on the other hand as HSI color model with light intensity I.

In various embodiments, the device for determining a homogeneity of complexion may include a data processing apparatus.

The data processing apparatus may be for example a computer, a tablet, a smartphone, a laptop or any other data processing apparatus that is able to perform the method for determining a homogeneity of complexion according to various embodiments. The data processing apparatus may include a processor, for example a microprocessor.

In various embodiments, the apparatus for determining a homogeneity of complexion may include a display apparatus.

The display apparatus may include for example a screen of a smartphone, of a desktop computer, of a laptops or of some other apparatus for determining a homogeneity of complexion. The display apparatus may be used for example to display results of the method for determining a homogeneity of complexion or the individual guide, prompt for the entry of input parameters for carrying out the method, or similar. Alternatively, the results of the method for determining a homogeneity of complexion or the individual guide may be presented by voice output. Accordingly, input parameters for carrying out the method may be supplied to the method by voice input. The voice input may be carried out via a microphone and the voice output may be assured with a loudspeaker.

The results of the method for determining a homogeneity of complexion, particularly the homogeneity value, may be indicated in the form of a quantitative measure. This may be a percentage, for example, or a dimensionless figure.

The display apparatus may be connected to the data processing apparatus via a first data link. The display apparatus may exchange data with the data processing apparatus via the first data link. In the event that the apparatus for determining a homogeneity of complexion includes a smartphone, a tablet or the like, the display apparatus and the first data link may be integrated in the apparatus.

In various embodiments, the apparatus for determining a homogeneity of complexion may include a camera.

According to various embodiments, the camera may be configured to capture a digital image of skin, e.g., the skin of a user.

According to various embodiments, the at least one camera may include a digital photographic camera or a video camera, i.e. a camera that can be configured to record a plurality of individual images in a temporal sequence.

In various embodiments apparatus for determining a homogeneity of complexion may include a second data link between the computer and the camera. Data may be transferred from the computer to the camera via the second data link, for example, for a conventional software control of the camera, for example. In addition, it may be possible to transmit data, for example the single or multiple digital images captured by the camera to the computer via the second data link. In a case in which the apparatus for determining a homogeneity of complexion includes a smartphone, a tablet or similar, the camera and the second data link may be integrated in the apparatus for determining a homogeneity of complexion.

In various embodiments, a camera may be omitted from the apparatus for determining a homogeneity of complexion, for example if the digital image is provided to the data processing apparatus in another way, for example by data transmission.

The data processing apparatus may be configured with an image processing software program, using a processor for example, to process the image received from the camera or otherwise, in order to determine the skin display area in the received image in known manner, for example and, as described previously for various embodiments, to determine the homogeneity of complexion. In various embodiments the image processing software may include an app.

In various embodiments, the data processing apparatus may include an input apparatus for providing information to the data processing apparatus, for example a keyboard, a mouse, a touch-sensitive surface of the display apparatus or similar.

The input apparatus may be connected to the data processing apparatus via a third data link. The input apparatus may exchange data with the data processing apparatus via the third data link. In a case in which the apparatus for determining a homogeneity of complexion includes a smartphone, a tablet or similar, the input apparatus and the third data link may integrated in the apparatus for determining a homogeneity of complexion.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining a homogeneity of skin color, comprising the steps of:

providing a digital image, on which skin is portrayed and which is parameterized in a color space which is defined by a parameter set in which one of the parameters is a hue;

identifying and/or defining at least one skin examination area in the digital image;

calculating a hue distribution in the at least one skin examination area; and determining at least one homogeneity value for the skin color based on the calculated hue distribution, wherein:

the hue is defined by a color angle on a color circle, the determining of the at least one homogeneity value based on the determined hue distribution includes determining a circular variance, and the circular variance has a value that is always between 0 and 1.

2. The method according to claim 1, wherein the providing of the digital image includes a transformation of an original digital image which has been parameterized in an original color space into the color space, wherein the original color space is different from the color space.

3. The method according to claim 1, wherein the color space is a hue-saturation-brightness color space.

4. The method according to claim 1, wherein the identifying and/or defining of the at least one skin examination area includes defining the at least one skin examination area by a user.

5. The method according to claim 4, wherein the defining of the at least one skin examination area by the user includes defining a position and/or a shape and/or a size of the at least one skin examination area.

6. The method according to claim 1, wherein the identifying and/or defining of the at least one skin examination area includes:

determining a skin display area in which the skin is displayed; and defining at least a part of the skin display area as the at least one skin examination area.

7. The method according to claim 1, wherein the at least one skin examination area includes a plurality of skin examination areas each having a central point.

8. The method according to claim 7, wherein the plurality of skin examination areas differ from each other in respect of a position of the central points of the plurality of skin examination areas.

9. The method according to claim 8, further comprising the step of:
correlating the determined homogeneity value with the positions of the central points of the plurality of skin examination areas.

10. The method according to claim 1, further comprising the step of:
displaying a result of the determining of the homogeneity of skin color.

11. The method according to claim 10, wherein the displaying of the result includes displaying the digital image, wherein the skin is displayed in a skin display area of the digital image with the hue, wherein the entire skin display area is displayed with a uniform color saturation and a uniform brightness.

12. The method according to claim 1, further comprising the step of:
displaying an individual guide based on the at least one homogeneity value, the individual guide including one or more of:
skin care product recommendations,
individual skin cleansing instructions, and/or
individual skin care instructions.

13. A device for determining a homogeneity of complexion, the device comprising:
a display apparatus; and
a data processing apparatus in operable communication with the display apparatus, the data processing apparatus including a processor that is configured to:
receive a digital image, on which skin is portrayed and which is parameterized in a color space which is defined by a parameter set in which one of the parameters is a hue that is defined by a color angle on a color circle;
identify and/or define at least one skin examination area in the digital image;
calculate a hue distribution in the at least one skin examination area; and
determine at least one homogeneity value for the skin color based on the calculated hue distribution by determining a circular variance,
wherein the circular variance has a value that is always between 0 and 1.

14. The device of claim 13, further comprising:
a camera in operable communication with the processor, the camera configured to capture and supply the digital image to the processor.

* * * * *